(12) United States Patent
Rognlien et al.

(10) Patent No.: US 9,880,062 B1
(45) Date of Patent: Jan. 30, 2018

(54) ENVIRONMENT SENSOR FOR ACOUSTIC INSTRUMENT

(71) Applicant: Music Nomad LLC, Sonoma, CA (US)

(72) Inventors: Rand Rognlien, Sonoma, CA (US); Pieter Hans Schouten, Berkeley, CA (US)

(73) Assignee: Music Nomad LLC, Sonoma, CA (US)

( * ) Notice: Subject to any disclaimer, the term of this patent is extended or adjusted under 35 U.S.C. 154(b) by 0 days.

(21) Appl. No.: 15/352,036

(22) Filed: Nov. 15, 2016

Related U.S. Application Data

(63) Continuation of application No. 14/996,138, filed on Jan. 14, 2016, now Pat. No. 9,518,949.

(60) Provisional application No. 62/103,292, filed on Jan. 14, 2015.

(51) Int. Cl.
  *G10G 7/00* (2006.01)
  *G01K 13/00* (2006.01)
  *G01N 33/00* (2006.01)

(52) U.S. Cl.
  CPC .......... *G01K 13/00* (2013.01); *G01N 33/0036* (2013.01); *G10G 7/00* (2013.01)

(58) Field of Classification Search
  CPC ..................................................... G10G 7/00
  See application file for complete search history.

(56) References Cited

U.S. PATENT DOCUMENTS

| | | | | |
|---|---|---|---|---|
| 3,407,700 A * | 10/1968 | Hollander | ............... | G10G 7/00 239/55 |
| 3,721,152 A * | 3/1973 | Von Meyer | .............. | G10D 3/00 239/55 |
| 4,572,051 A * | 2/1986 | Laskin | ..................... | G10G 7/00 239/57 |
| 4,649,793 A * | 3/1987 | Blackshear | ............. | G10D 3/00 84/453 |
| 6,209,717 B1 * | 4/2001 | Flynn | .................... | G10G 7/005 206/204 |
| 7,028,914 B1 * | 4/2006 | Mair | ........................ | F24F 6/00 236/44 A |
| 8,087,645 B2 * | 1/2012 | Hepple | .................... | G10G 7/00 261/104 |
| 8,220,782 B2 * | 7/2012 | Hepple | .................... | G10G 7/00 239/35 |
| 9,518,949 B1 * | 12/2016 | Rognlien | ............... | G01K 13/00 |
| 9,568,203 B1 * | 2/2017 | Small | ........................ | F24F 6/06 |
| 9,613,604 B1 * | 4/2017 | Shearer | .................... | G10G 7/00 |
| 2006/0226037 A1 * | 10/2006 | Field | ..................... | A45C 15/00 206/314 |

(Continued)

*Primary Examiner* — Robert W Horn
(74) *Attorney, Agent, or Firm* — Bond Schoeneck & King, PLLC; George McGuire

(57) ABSTRACT

A system and method for enabling measurement of desired environmental criteria of an instrument during storage, including in some situations storage within a closely conforming instrument case. A humireader includes a planar body forming a "T" with a support face. The support face enables a user to suspend and support the body between a pair of adjacent strings allowing the body to extend through a sound hole. An environment sensing system disposed within the body collects environment data of the instrument and presents it to the user using an output system (e.g., a display) that is part of the support face.

20 Claims, 9 Drawing Sheets

(56) References Cited

U.S. PATENT DOCUMENTS

| | | | |
|---|---|---|---|
| 2010/0012739 A1* | 1/2010 | Hoeth | G10G 7/00 236/44 C |
| 2013/0112764 A1* | 5/2013 | Chan | G10D 3/00 236/44 C |
| 2016/0042726 A1* | 2/2016 | Glaser | G10G 7/005 705/4 |

* cited by examiner

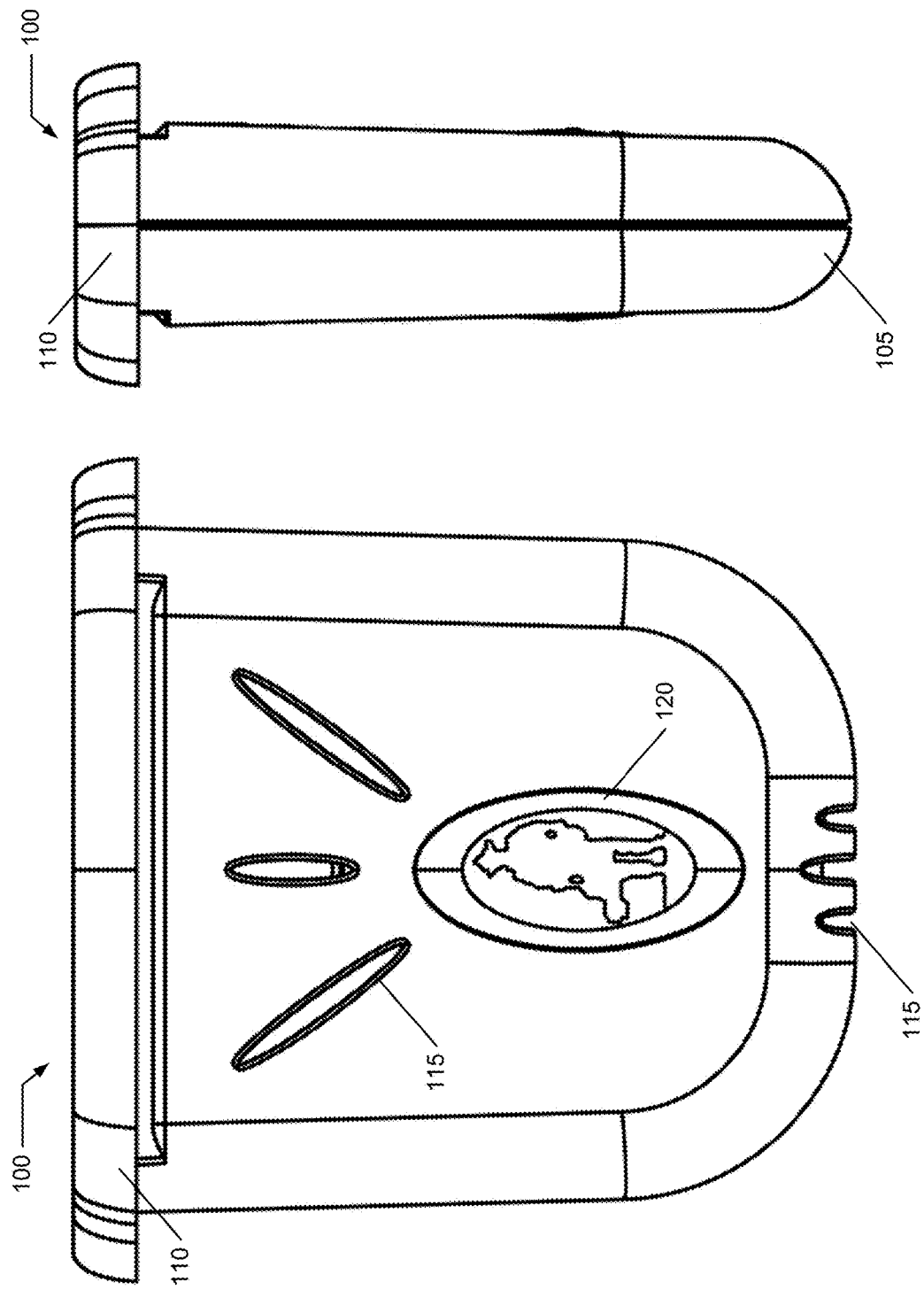

ENVIRONMENT SENSOR FOR ACOUSTIC INSTRUMENT

CROSS REFERENCE TO RELATED APPLICATIONS

This application is a continuation of U.S. patent application Ser. No. 14/996,138 filed 14 Jan. 2016 which in turn claims benefit of U.S. Patent Application No. 62/103,292, the contents of which are hereby expressly incorporated by reference thereto in their entireties for all purposes.

FIELD OF THE INVENTION

The present invention relates generally to an environmental sensor, and more specifically, but not exclusively, to an environmental sensor configured for use with an acoustic instrument having a resonant cavity accessed through a sound hole, the sensor supported by one or more instrument structures into the sound hole for collection of environmental data.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Wooden acoustic instruments are made from solid wood components or from layered wood components. It is recognized that such musical instruments are desirably maintained within an environment having certain specified criteria, such as for example, for humidity and/or temperature. Storing the instrument outside of these criteria can adversely affect sound quality and/or instrument life.

An acoustic wooden instrument typically defines a soundbox having an internal cavity and one or more sound holes. Environmental conditions of the soundbox are often the most important with measurement of the environmental criteria of the soundbox the most critical.

For those times that the instrument is not being operated, it is stored in many different ways. For example when considering a guitar, it is possible to store the guitar on a guitar stand, hung from a wall, or stored within a guitar case. Currently it is possible to collect some environmental data from the room where the instrument is stored. However, it is not always possible to provide an environmentally controlled storage facility. When it is possible, the collected data does not necessarily reflect the environmental condition within the sound hole.

For many wooden acoustic instruments, it is desirable to store them within custom instrument cases that include an interior cavity that conforms quite closely to external dimensions of the instrument.

What is needed is a system and method for enabling measurement of desired environmental criteria of an instrument during storage, including in some situations storage within a closely conforming instrument case.

BRIEF SUMMARY OF THE INVENTION

Disclosed is a system and method for enabling measurement of desired environmental criteria of an instrument during storage, including in some situations storage within a closely conforming instrument case. The following summary of the invention is provided to facilitate an understanding of some of technical features related to monitoring of environmental criteria of a wooden acoustic instrument, and is not intended to be a full description of the present invention. A full appreciation of the various aspects of the invention can be gained by taking the entire specification, claims, drawings, and abstract as a whole. The present invention is applicable to other wooden acoustic instruments in addition to guitars having a set of strings deployed near a sound hole.

For wooden acoustic instruments that include one or more strings positioned proximate a sound hole, an embodiment of the present includes an environment sensing system that designed to be positioned close to, or disposed within, the sound hole while being supported from one or more of the strings. The environment sensing system measures a set of environmental data such as, for example, humidity and/or temperature, of the instrument from the position at, near, or within the sound hole. The environment sensing system is supported at its desired location from one or more of the strings.

In an illustrated embodiment, the environment sensing system is disposed in a generally planar body having a maximum thickness less than a spacing between adjacent strings. The body of this embodiment is otherwise sized to fit within the sound hole of the instrument. A support face is coupled to the body generally perpendicular to the plane defined by the planar body. The support face of the illustrated embodiment includes a minimum width that exceeds the spacing between adjacent strings. In this way, the support face straddles a pair of adjacent strings above a portion of the sound hole with the planar body extending between the pair of adjacent strings toward, at, or within the sound hole. The support face and the planar body producing in combination a "T" configuration.

One use of an embodiment of the present invention is to allow an operator to store their wooden instrument in a closely conforming case, add the sensing system to the instrument, activate the device, and close the lid. The operator need only periodically open the lid of the case to check on the environmental conditions being monitored. For some implementations, it is desirable to have the sensing system not add appreciable stress to the system, such as unduly bowing the strings during storage because a portion of the sensor system includes a body having a width that exceeds the string spacing. In this case, the strings are bowed outward during storage. In some instances, it is preferred if the width were less than the spacing between adjacent strings. In other instances, a slight bowing may be acceptable or allowed, for example less than 10% of the string spacing, less than 5% of the string spacing, and less than 1% of the string spacing. In other implementations, it may be desirable to intentionally have the width greater than the spacing width to help secure the sensing system to the instrument and a bowing of greater than 10% may be desired.

In some embodiments, the environment sensing system includes a battery operated electronics circuit that includes one or more sensors and control system sample and measure desired environmental conditions. The support face includes a display on a flat surface generally perpendicular to the body and visible while the body is installed at its operational site. The display presents information regarding device operation and environment readout data. When installed, a user may monitor the desired environmental data by directly viewing the supported display.

In some embodiments, a "head" of the support face (i.e., a portion of the support face that extends above the strings when supporting an installed body) includes a shallow profile. This shallow profile enables an embodiment to be deployed within an instrument that, in turn, is stored within a conforming instrument case. A lid of the conforming case may closed with the embodiment installed in position in the instrument. The user may simply read environmental conditions of the instrument that are presented on the display by simply opening the lid of the case.

An instrument environmental sensor for a musical instrument including a body having one or more walls defining an internal cavity accessed through a sound hole having a set of size dimensions, has a body including a sensor, the body configured to extend into the sound hole so as to position the sensor proximate the internal cavity; and a mount, coupled to the musical instrument, configured to support the body with the sensor proximate the internal cavity.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 2 illustrates a front elevation view of the humireader of FIG. 1;

FIG. 3 illustrates a right hand side elevation view of the humireader of FIG. 1, the left hand side elevation view being a mirror image;

DETAILED DESCRIPTION OF THE INVENTION

Figure 1:
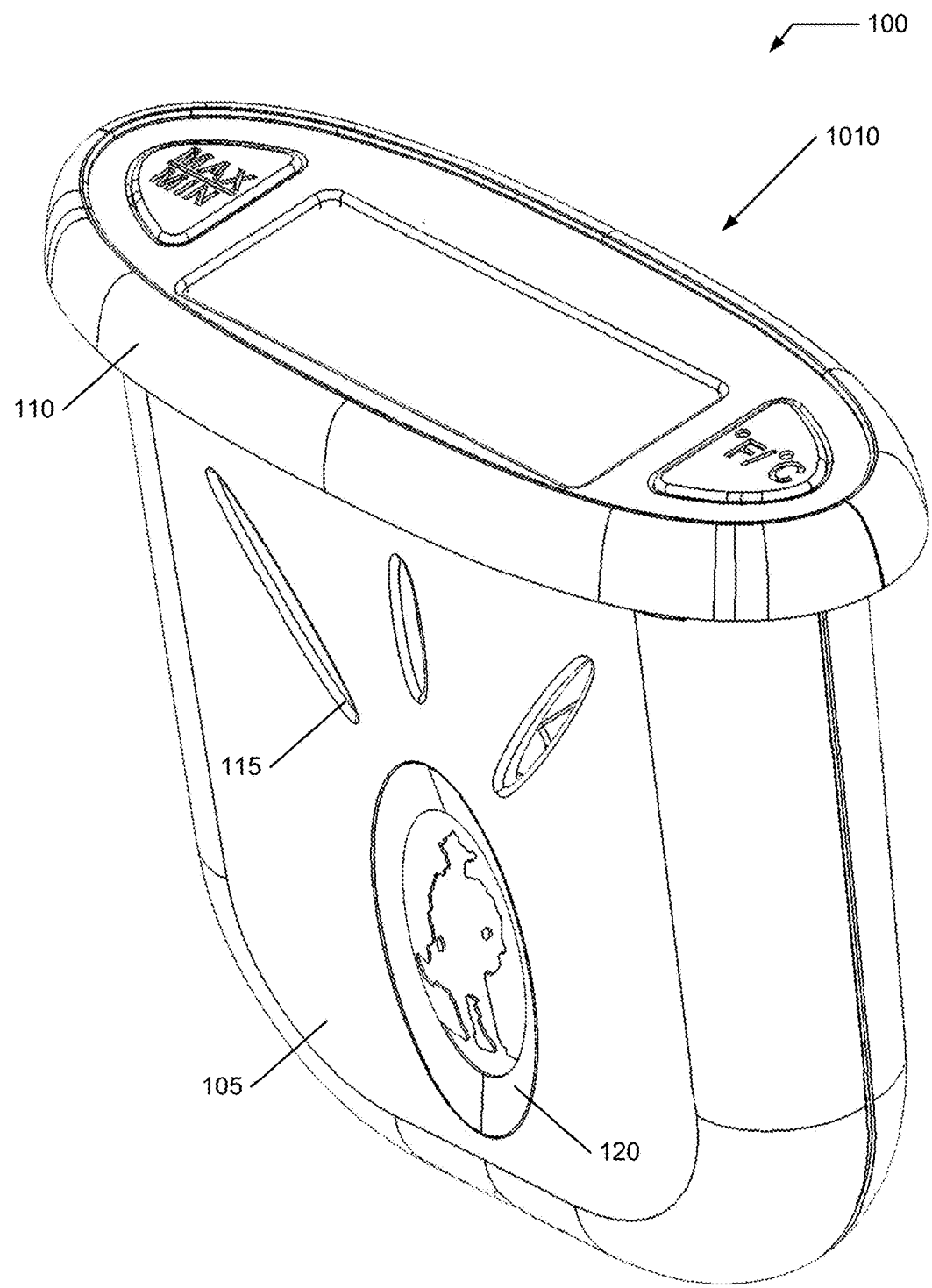
FIG. 1 illustrates an perspective view of a humireader.

Embodiments of the present invention provide a system and method for enabling measurement of desired environmental criteria of an instrument during storage, including storage within a closely conforming instrument case. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

The present invention is broadly applicable to stringed wooden acoustic instruments. To simplify the following the discussion, a guitar (e.g., a Taylor, Martin, or classical guitar) is used as a representative instrument to provide context for the invention (it being understood that the following description may benefit from specific adaptation to a specific instrument other than the guitar.

In this context, a guitar is a wooden acoustic instrument that produces sound by having one or more strings plucked. This sound is amplified by a soundboard and a resonant cavity, the resonant cavity accessed through a sound hole. Typically a guitar includes six or more strings that are nylon-based (e.g., may include a metal wrap) that produce lower tension than all metal strings.

The body of the guitar includes a top (the soundboard) that is often a thin (e.g., 2-4 mm thick) piece of wood that is internally braced. The body further includes sides and a bottom that, together with the soundboard, produce the resonating soundbox that projects vibrations of the body through a sound hole. This allows the guitar to be heard without powered amplification. The sound hole is traditionally a single round hole in the sound board (under the strings) though the number, type, size(s), and placement(s) can vary.

For purposes of this application, a guitar-class musical instrument is of this class of instrument having a body with a sound hole and a neck extending to a headstock. A set of strings are supported by a bridge on the body and extend to the headstock, along the neck and overlay the sound hole.

It is common to store the guitar-class musical instrument in an instrument case customized for the particular class or style. These instrument cases are typically closely conforming and have an interior volume shaped to closely match the exterior surfaces of the musical instrument, usually less than an inch, less than three-quarters or an inch, or less than one-half inch, or less than one-quarter inch margin is sometimes provided. This conformance usually applies to the closure system which often has a moveable door panel that swings open and shut. When open, the interior volume is exposed and the musical instrument is designed to be placed within the interior volume with the top surfaces of the body, neck, strings, and headstock exposed. There is often little clearance (this margin explained herein) between the door and the top surfaces when the door is closed. Embodiments of the present invention include size features to fit within these margins and be stored with the instrument installed in the case and the door closed. Simply opening the door allows a user interface to be accessed to review sensor data, such as for environmental conditions which may include temperature and humidity of an interior of the musical instrument as measured through an extension into the musical instrument through the sound hole. The sensing system may be supported by the overlying strings, or some other mechanical support coupled to the body proximate the sound hole.

Figure 4:
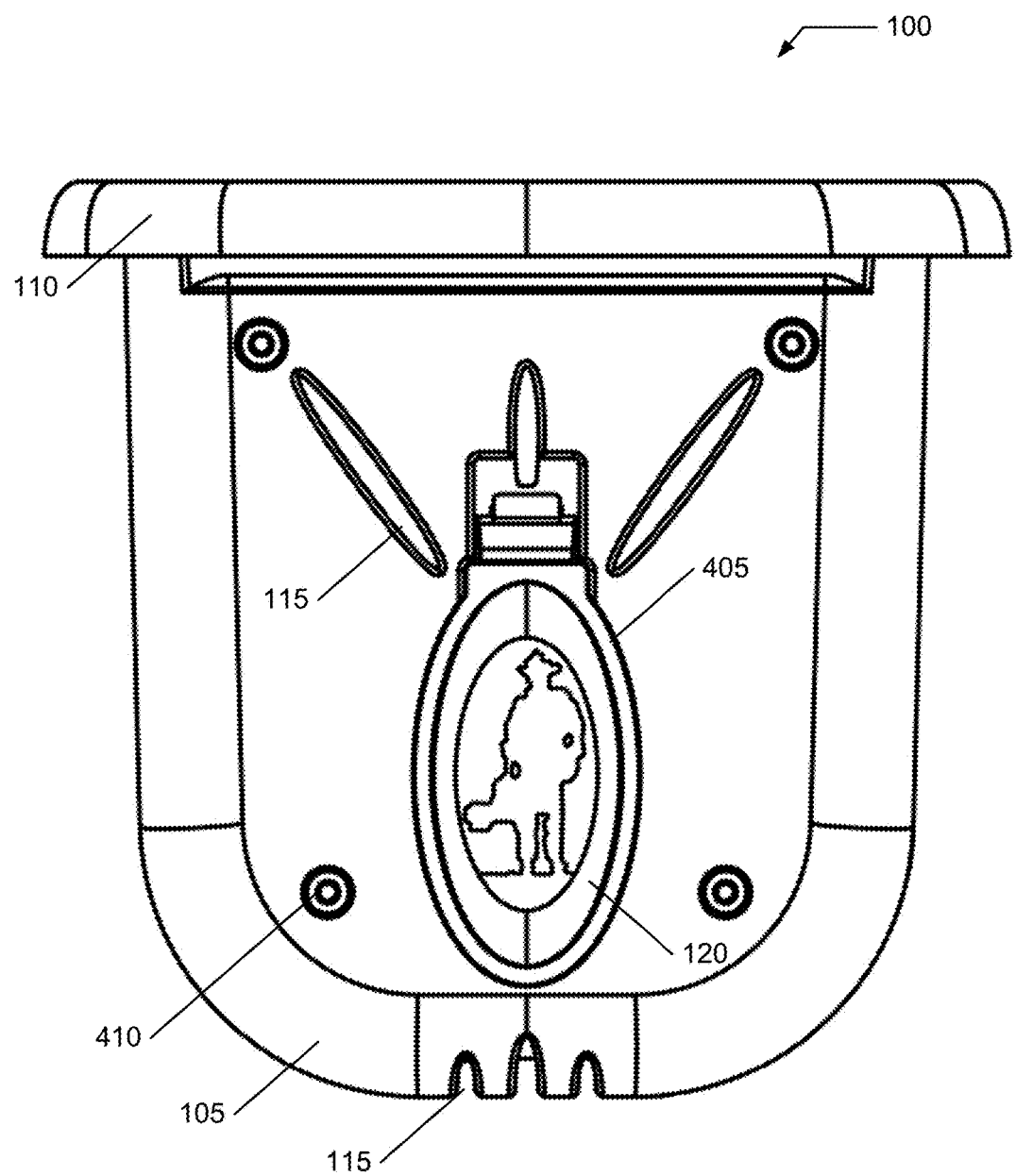
FIG. 4 illustrates a rear elevation of the humireader of FIG. 1.
Figure 5:
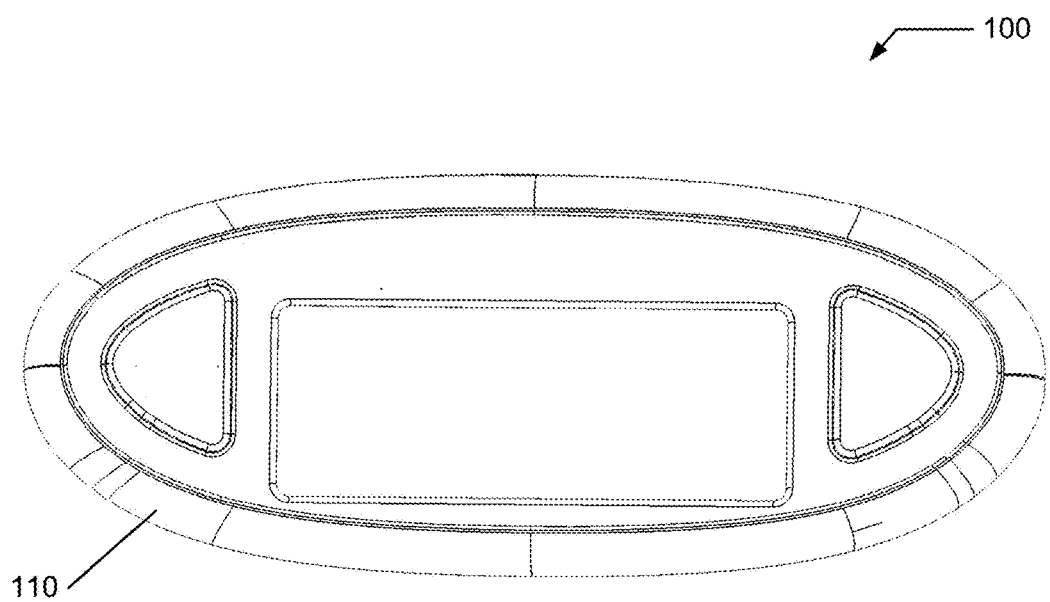
FIG. 5 illustrates a top plan view of the humireader of FIG. 1.
Figure 6:
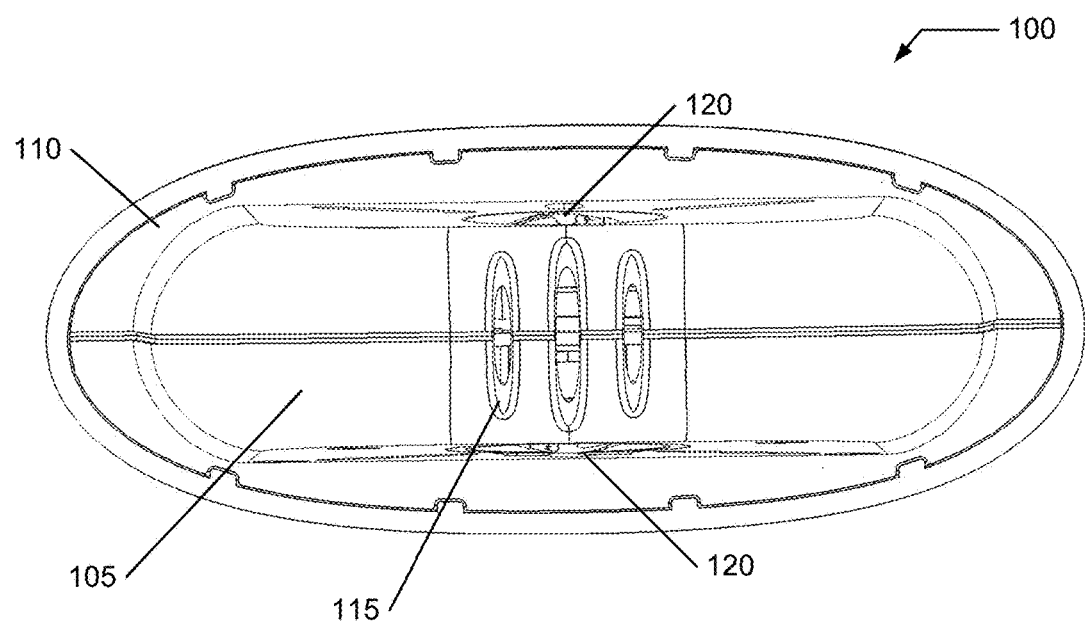
FIG. 6 illustrates a bottom plan view of the humireader of FIG. 1.

FIG. 1 illustrates an perspective view of a humireader 100; FIG. 2 illustrates a front elevation view of humireader 100; FIG. 3 illustrates a right hand side elevation view of humireader 100, the left hand side elevation view being a mirror image; FIG. 4 illustrates a rear elevation view of humireader 100; FIG. 5 illustrates a top plan view of humireader 100; and FIG. 6 illustrates a bottom plan view of humireader 100.

Humireader 100 includes a planar body 105 generally perpendicularly coupled to a support face 110. Body 105 has a maximum thickness designed to be less than a spacing of a pair of adjacent strings of a music instrument (or class of instrument). It is understood that the spacing of the strings may vary somewhat not only due to construction and instrument implementation details, but also because the strings are designed to move relative to one another and deviate from an unmanipulated at rest position. Thus there is some allowance for the thickness to be greater than this "at rest" spacing with body 105 maintaining a pair of adjacent strings in this separated mode for as long as it is deployed between the strings.

It is also possible to control a length of body 105 which, depending upon implementation, controls to what degree portions of body 105 extend toward, at, or within the sound hole or instrument soundbox cavity through the sound hole. Some embodiments are enabled to extend deep within the sound hole for accurate environment measurements of the conditions within the soundbox.

Body 105 may be manufactured from a range of suitable materials that may secure and protect an environmental sensing system disposed within (not shown). For example, any mineral, plant, and/or metal material, including natural or man-made polymers and/or elastomers may be used in the construction of body 105. Body 105 includes a top, a bottom, and one or more sidewalls that extend between the top and the bottom. The one or more sidewalls may define a number of apertures 115 such as used to provide ambient environment of body 105 to be sensed and measured by the environment sensing system. An optional logo 120 may be also presented on body 105.

Face 110, in contrast, includes a width designed to be greater than this spacing. This allows face 110 to be supported by the pair of adjacent strings above the sound hole with body 105 suspended therebetween. By having body 105 with a thickness greater than the "at rest" spacing of the pair of adjacent strings, installation of humireader 100 spreads these strings and maintains them in the displaced locations. A force acting on the strings to return them to the at rest spacing can act as a holding force to help maintain humireader 100 in place during manipulations of the instrument.

Not all embodiments are required to have this arrangement for support face 110. In some embodiments, support face 110 may be configured to suspend from a single string by a clip, hook, or some other mechanical interface coupled to body 105 and associated with support face 110

In the illustrated embodiments, humireader 100 includes a generally "T" shaped configuration with body 105 and support face 110 generally at right angles. As the strings of a music instrument having a sound hole are generally parallel to a top surface of the instrument, the T shape allows an exposed top surface to be generally parallel to the top surface as well such that any plan view of the instrument in storage allows the display of humireader 100 to be easily read at the same time. This information read may very accurate as it is based upon information collected from a sensing system within body 105 that may be positioned deep within the sound hole. This is one way in which humireader 100 is a simple and efficient device for helping a caretaker of an instrument properly monitor actual important in-instrument environmental conditions.

An optional battery door 405 for installation and replacement of batteries is illustrated in FIG. 4. Additionally, FIG. 4 includes optional connectors 410 (e.g., rivets) for closing body 105.

Figure 7:
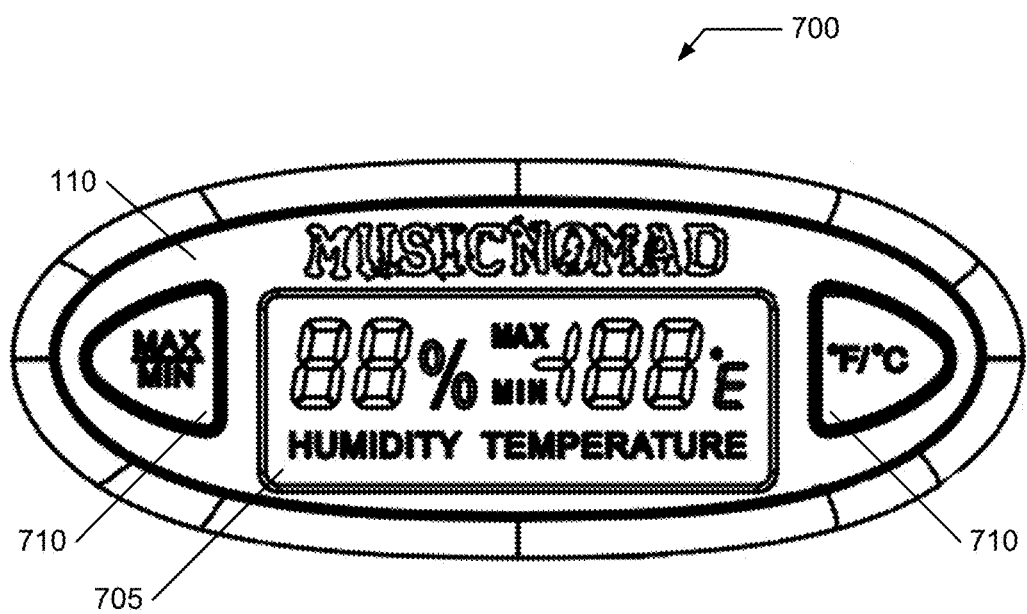
FIG. 7 illustrates a representative interface.

FIG. 7 illustrates a representative interface 700 for humireader 100, such as may be available on a flat exposed surface of support face 110 illustrated in FIG. 1-FIG. 6. Interface 700 may include desired interface elements, for example a display 705 and a pair of interface buttons 710.

As noted herein, body 105 of humireader 100 includes an environment sensing system that includes one or more environmental sensors. Some embodiments include a printed circuit board (PCB) that supports a controller and the one or more environmental sensors. The controller may be a stored program computer that executes program instructions accessed from a memory to meet operational design parameters. Those parameters include measurement and display of environment sensor data/measurements. The output may be provided via display 705. For example, the environment sensing system may include one or more sensors for humidity and/or temperature. The measured sensor data is presented on display 705.

Some embodiments may provide additional features or functions that respond to user selection. An input system may be implemented using interface buttons 710 enabling the user to select desired options from available options. For example, one button 710 may enable a user to set a min and max value for one or more of the sensed parameters (e.g., humidity). Some systems may include an alarm or notification feature that is triggered based upon a comparison of a measured value against the user-set min and/or max values.

Another interface button 710 may allow a user to set units for the data presented on display 705. For example, a user may be able to select a Fahrenheit scale or a Celsius scale for temperature readings. Some implementations may provide for a wireless interface instead, such as a low energy Bluetooth communication system, WiFi, or radiofrequency (RF) network-capable communications system. Such an interface may be paired with another device, for example, a smart phone or other portable electronic device that includes an operating environment supporting an application that enables a user to remotely monitor environmental data. In some implementations, display 705 and interface buttons 710 may be eliminated to allow all controls to be defined/set by the application, and to provide data readout on the application. A single application may be adapted to monitor one or more humireaders configured in this way.

Figure 8:
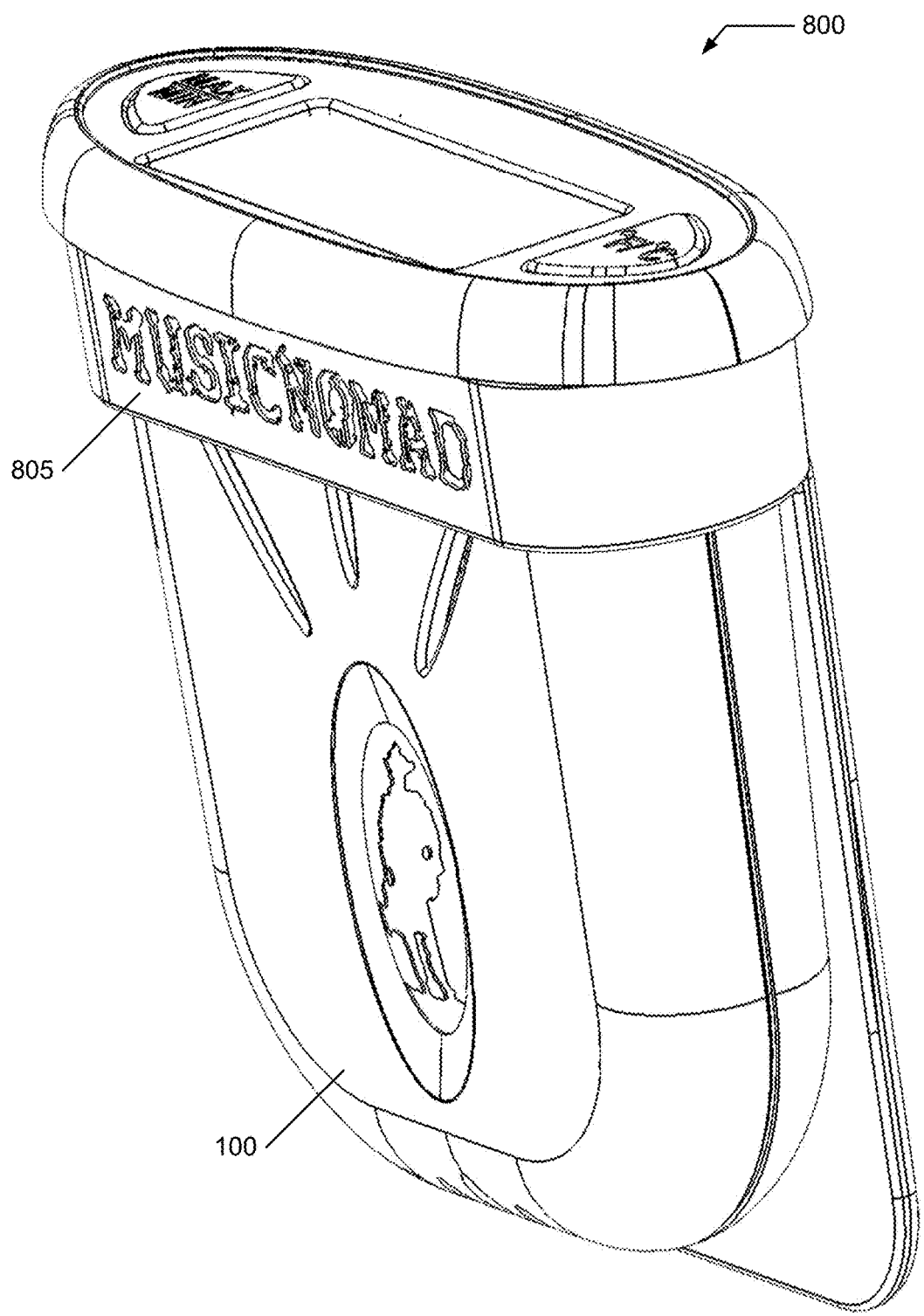
FIG. 8 illustrates a perspective view of the humireader of FIG. 1 disposed within a representative humireader holster.
Figure 9:
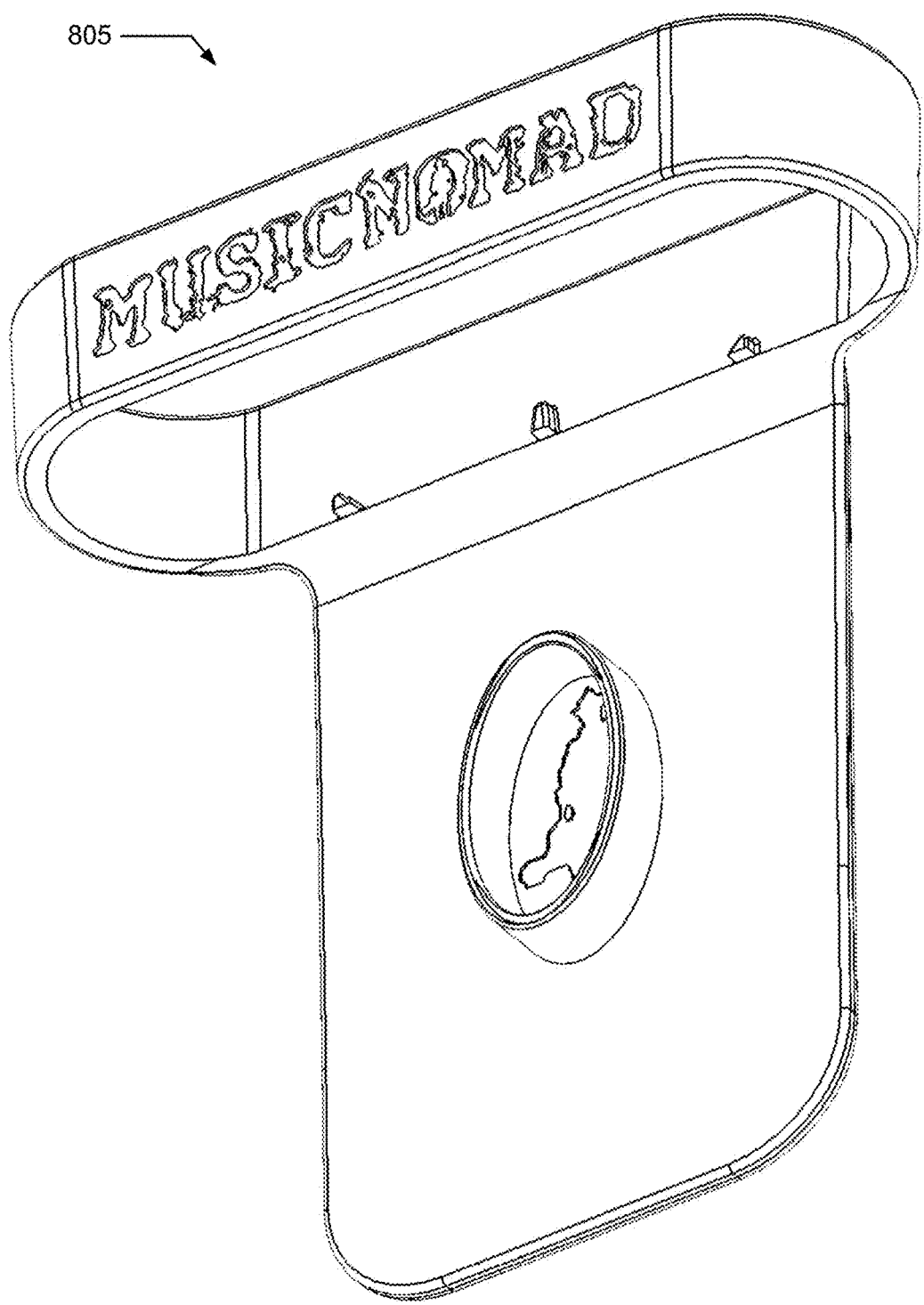
FIG. 9 illustrates a perspective view of the humireader holster illustrated in FIG. 8.

FIG. 8 illustrates a perspective view of a system 800 including humireader 100 disposed within a representative humireader holster 805; and FIG. 9 illustrates a perspective view of humireader holster 805. Humireader holster 805 may be mounted to a structure (wall, instrument case, or the like) that is close to the instrument to be monitored. The holster enables a humireader 100 to be secured in place having an environment to be monitored. Holster 805 may be secured to the structure permanently or semipermanently to allow the humireader to be stored into holster 805, and removed from holster 805, easily. Holster 805 allows a stored humireader 100 to be oriented in manner in which any display is easily read during use. In cases where humireader 100 is not easily read, that it is easily removed and viewed/read provides further versatility for a user.

Figure 10:
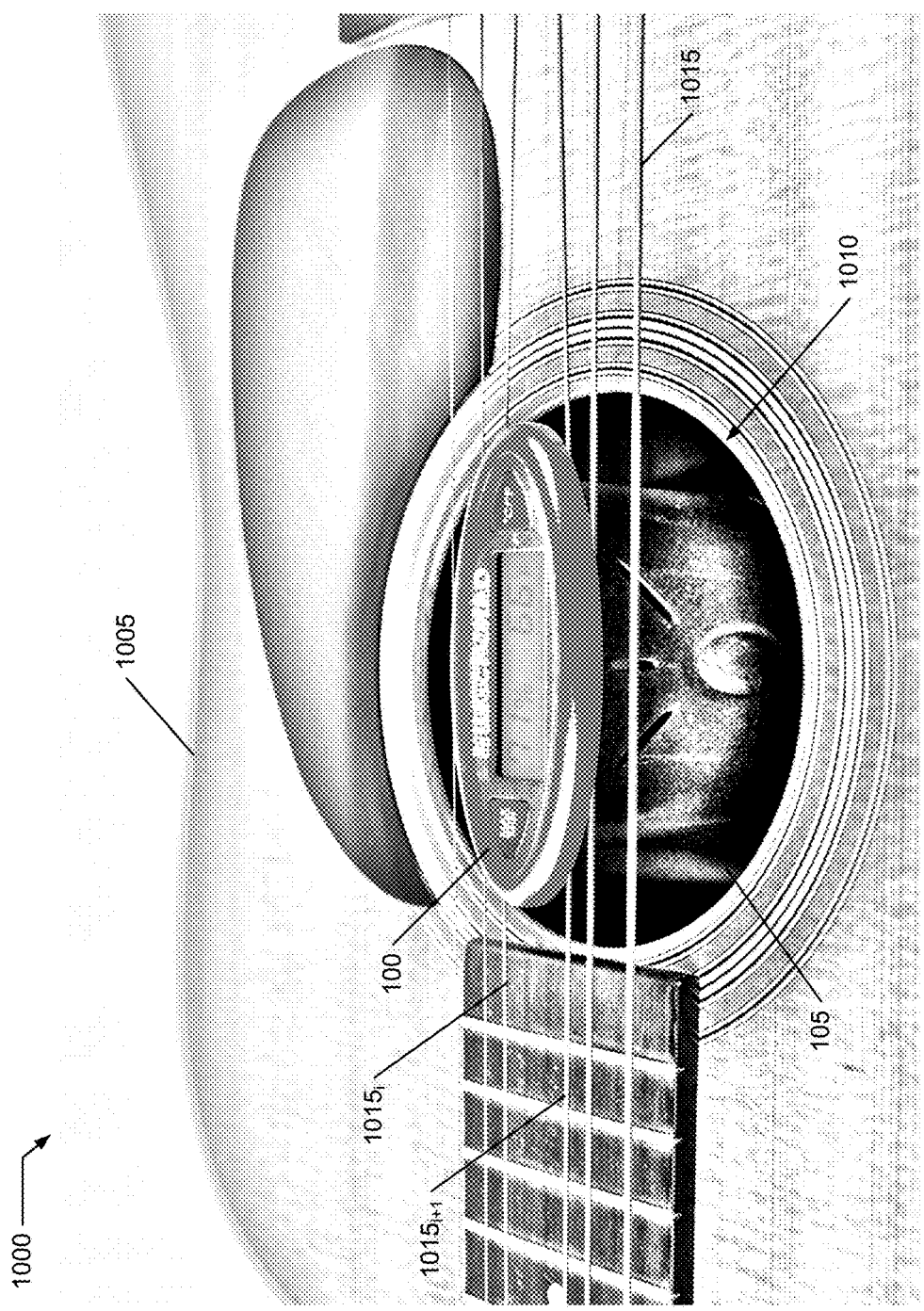
FIG. 10 illustrates a portion of a wooden acoustic instrument including a sound hole with the humireader of FIG. 1 suspended from a pair of neighboring strings and extending into the sound hole.

FIG. 10 illustrates a system 1000 including a portion of a wooden acoustic instrument 1005 including a sound hole 1010. System 1000 includes humireader 100 suspended from a pair of neighboring strings 1015 (e.g., a string $1015_i$ and a string $1015_{i+1}$) and having body 105 extending into sound hole 1010.

Figure 11:
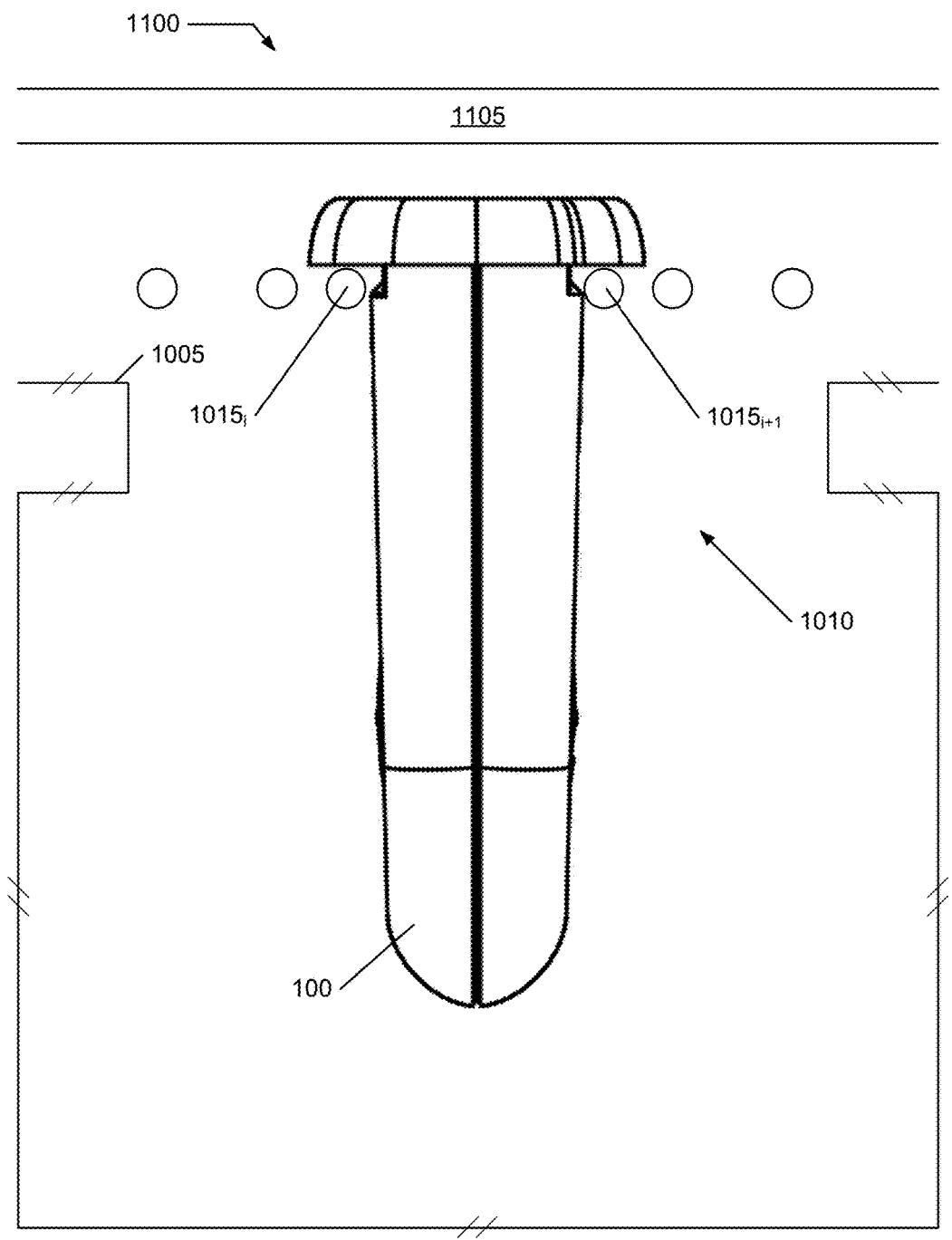
FIG. 11 illustrates a sectional view of the portion of the wooden acoustic instrument supporting the humireader by a pair of adjacent strings inside the sound hole with an overlying closed case cover.

FIG. 11 illustrates a sectional view of a storage system 1100 including system 1000 disposed in a conforming instrument case with an overlying closed case cover 1105. As noted herein, humireader 100 may be used in cooperation with an appropriate acoustic instrument irrespective of whether it is stored in a conforming instrument case. It is a feature of the present invention that some embodiments may be adapted for use in an instrument stored in a conforming instrument case such as represented in FIG. 11. The configuration and arrangement of system 1000 allows a height of a head of humireader 100 to be less than a spacing between a top of strings 1015 and a bottom of case cover 1105. In this way, case cover 1105 is easily closed and case latched/locked to secure and protect the instrument. For embodiments designed for an in-case deployment concurrent with in-instrument installation, the height is less than 20 mm, and preferably less than 10 mm, and most preferably less than 7 mm above strings 1015.

The system and methods above has been described in general terms as an aid to understanding details of preferred embodiments of the present invention. In the description herein, numerous specific details are provided, such as examples of components and/or methods, to provide a thorough understanding of embodiments of the present invention. While some disclosed embodiments include a "T-shaped" sensing system in which "arms" of the "T" straddle a pair of strings to suspend the body of the "T" into the sound hole, there are other alternatives to supporting the body by a mechanism other than these arms. Some embodiments may include a clip or other mechanical fastener/holder to support the body above, at, near, or inside the sound hole. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An instrument environmental sensor for a musical instrument including a housing having one or more walls defining an internal cavity accessed through a sound hole having a set of size dimensions, comprising:
    a body including a powered sensor, said body configured to extend into the sound hole so as to position said powered sensor proximate the internal cavity; and
    a mount, coupled to the musical instrument, configured to support said body with said sensor proximate to the internal cavity.

2. The instrument environmental sensor of claim 1 wherein the musical instrument includes a set of strings supported over the sound hole a height distance and outside of the internal cavity, wherein a pair of adjacent strings of the set of strings have a spacing distance between them, wherein said body includes an elongate portion with a proximal end and a distal end opposite of said proximal end and having a body distance between said ends that is greater than said height distance, wherein said mount is coupled to said proximal end, wherein said sensor is disposed proximate said distal end, and wherein said mount engages said pair of adjacent strings.

3. The instrument environmental sensor of claim 2 wherein said elongate portion includes a body width that is less than said spacing distance with said elongate portion configured to suspend between said pair of adjacent strings without significantly bowing them laterally.

4. The instrument sensor of claim 1 wherein said sensor includes a humidity sensor.

5. The instrument sensor of claim 2 wherein said sensor includes a humidity sensor.

6. The instrument sensor of claim 3 wherein said sensor includes a humidity sensor.

7. The instrument sensor of claim 1 wherein said sensor includes a temperature sensor.

8. The instrument sensor of claim 2 wherein said sensor includes a temperature sensor.

9. The instrument sensor of claim 3 wherein said sensor includes a temperature sensor.

10. The instrument sensor of claim 4 wherein said sensor includes a temperature sensor.

11. The instrument sensor of claim 5 wherein said sensor includes a temperature sensor.

12. The instrument sensor of claim 6 wherein said sensor includes a temperature sensor.

13. The instrument sensor of claim 1 wherein said mount includes a support coupled at about a right angle to said body, said support generally planar.

14. The instrument sensor of claim 2 wherein said mount includes a support coupled at about a right angle to said body, said support generally planar and having a support width greater than said spacing distance wherein said support suspends said body portion from said set of strings.

15. The instrument sensor of claim 14 wherein said support includes a topmost exterior surface wherein said topmost surface has a height above said set of strings that does not exceed 20 millimeters.

16. The instrument sensor of claim 14 wherein said support includes a topmost exterior surface facing away from the musical instrument and wherein said topmost exterior surface includes a user interface with a set of input/output elements coupled to said sensor for presenting a set of environmental conditions of said internal cavity.

17. The instrument sensor of claim 15 wherein said support includes a topmost exterior surface facing away from the musical instrument and wherein said topmost exterior surface includes a user interface with a set of input/output elements coupled to said sensor for presenting a set of environmental conditions of said internal cavity.

18. A method for monitoring a set of environmental conditions present inside a musical instrument including a housing having one or more walls defining an internal cavity accessed through a sound hole having a set of size dimensions, wherein the musical instrument includes a set of strings supported over the sound hole at a height distance, and wherein a pair of adjacent strings of the set of strings have a spacing distance between them, comprising:

a) disposing a body portion over the sound hole and between the pair of adjacent strings wherein a distal end of said body portion extends into the sound hole, said distal end including an environmental sensor;
b) supporting said distal end within the sound hole using a support portion coupled to said body portion, said support portion coupled to the pair of adjacent strings and wherein said support portion includes a topmost exterior surface that extends no more than about 20 mm above the pair of adjacent strings;
c) activating said environmental sensor responsive to a user interface available at said topmost exterior surface;
d) placing the musical instrument within a closely conforming instrument case wherein said closely conforming instrument case includes a closure system that opens and closes a cover over the set of strings wherein the set of strings and sound hole are visible when said cover is opened and wherein said cover is proximate the set of strings when closed; and
e) closing the cover while said distal end is disposed within said sound hole and said body portion is supported by said support portion without interfering with closing the cover;
wherein said user interface is visible when said cover is opened, said user interface displaying a set of environmental conditions inside the internal cavity of the musical instrument.

19. An instrument environmental sensor for a stored musical instrument including a housing having one or more walls defining an internal cavity accessed through a sound hole having a set of size dimensions with the stored musical instrument including a set of strings overlying the sound hole and extending from the housing along a neck to a headstock, the stored musical instrument disposed within an instrument case having a closely conforming interior volume complementary to an exterior profile of the musical instrument, the instrument case including a moveable door to open and close over a set of top surfaces of the housing, the set of strings, the neck and the headstock, comprising:
an electronic environmental sensing system including a power source, a control, a user interface, and a sensor, said electronic environmental sensing system configured to measure a set of environmental conditions;
a body containing said electronic environmental sensing system, said body including a proximal end and a distal end opposite from said proximal end, said sensor disposed at said distal end, said body sized to present said distal end through the sound hole and dispose said sensor within the internal cavity; and
means, coupled to said proximal and to the musical instrument, for supporting said body with said sensor disposed within the internal cavity, said means for supporting said body including a top generally planar surface disposed above the set of strings and including at least a portion of said user interface;
wherein the means for supporting said body does not interfere with closing the moveable door while supporting said body with said sensor disposed within the internal cavity.

20. The instrument environmental sensor of claim 19 wherein said set of environmental conditions includes at least one of temperature or humidity or a combination thereof.

* * * * *